United States Patent
Holmström et al.

(10) Patent No.: US 7,330,758 B2
(45) Date of Patent: Feb. 12, 2008

(54) HEART MONITORING DEVICE, SYSTEM AND METHOD

(75) Inventors: Nils Holmström, Järfälla (SE); Anna Norlin, Stockholm (SE); Kenneth Dahlberg, Stockholm (SE); Martin Obel, Danderyd (SE)

(73) Assignee: St. Jude Medical AB, Jarfalla (SE)

( * ) Notice: Subject to any disclaimer, the term of this patent is extended or adjusted under 35 U.S.C. 154(b) by 585 days.

(21) Appl. No.: 10/396,843

(22) Filed: Mar. 25, 2003

(65) Prior Publication Data

US 2004/0015196 A1    Jan. 22, 2004

(30) Foreign Application Priority Data

Mar. 25, 2002    (SE) .................................... 0200922

(51) Int. Cl.
*A61N 1/365* (2006.01)
(52) U.S. Cl. .......................................... 607/17; 607/28
(58) Field of Classification Search ................ 607/24, 607/28, 17; 600/547
See application file for complete search history.

(56) References Cited

U.S. PATENT DOCUMENTS

| 4,450,527 | A | * | 5/1984 | Sramek ....................... 600/484 |
| 4,562,843 | A | * | 1/1986 | Djordjevich et al. ........ 600/485 |
| 4,733,667 | A | * | 3/1988 | Olive et al. .................... 607/24 |
| 5,154,171 | A | | 10/1992 | Chirife |
| 5,235,976 | A | | 8/1993 | Spinelli |
| 5,505,209 | A | | 4/1996 | Reining |
| 5,720,768 | A | | 2/1998 | Verboven-Nelissen |
| 5,824,019 | A | | 10/1998 | Rueter et al. |
| 6,070,100 | A | | 5/2000 | Bakels et al. |
| 6,490,486 | B1 | * | 12/2002 | Bradley ....................... 607/28 |
| 2001/0012953 | A1 | | 8/2001 | Molin et al. |
| 2001/0021864 | A1 | | 9/2001 | Molin et al. |

FOREIGN PATENT DOCUMENTS

| EP | 0 591 642 | 4/1994 |
| EP | 0 607 511 | 7/1994 |
| WO | WO 01/87410 | 11/2001 |

OTHER PUBLICATIONS

"An Abnormal Early Diastolic Impedance Wave Form: A Predictor Of Poor Prognosis in the Cardiac Patient?," Ramos, American Heart Journal, vol. 94, No. 3 (Sep. 1977) pp. 274-281.

(Continued)

*Primary Examiner*—George Evanisko
*Assistant Examiner*—Michael Kahelin
(74) *Attorney, Agent, or Firm*—Schiff Hardin LLP

(57) ABSTRACT

A heart monitoring device has a control circuit that derives an impedance value indicative of the impedance between different electrode surfaces. The control circuit determines and monitors a negative rate of change of the impedance value and determines whether the negative rate of change, or its absolute value, increases or decreases over a number of heart cycles. Alternatively or additionally, the control circuit may determine and monitor a relationship between a positive rate of change and a negative rate of change of the impedance value. The device can, in particular, be used to detect and treat a diastolic dysfunction of a heart.

39 Claims, 4 Drawing Sheets

OTHER PUBLICATIONS

"A Comparison of Bioimpedance and Echocardiography in Measuring Systolic Heart Function in Cardiac Patients, Kerkkamp et al", Annals of the New York Academy Sciences, vol. 873 (1999) pp. 149-154.

"Do Changes in Transcardiac Impedance Modulation Correlate with Haemodynamic Status?", Weiss et al., Australian Physical and Engineering Science in Medicine, vol. 15, No. 2, (1992) pp. 57-64.

* cited by examiner

HEART MONITORING DEVICE, SYSTEM AND METHOD

RELATED APPLICATION

The present application is related to co-pending application Ser. No. 10/396,958, filed simultaneously herewith ("Heart Monitoring Device, System and Method," Holmström et al.).

BACKGROUND OF THE INVENTION

1. Field of the Invention

The present invention relates to a heart monitoring device, AS WELL AS to a system including such a device and to a manner of using the system. The device is of the type used to monitor the performance of a heart of a human or animal being. The device may also be able to deliver electrical stimulation pulses to the heart.

2. Description of the Prior Art

Several different devices for monitoring the performance of a heart are known. Often these devices also are able to deliver stimulation pulses to the heart. Such heart stimulation devices, or pacers, are normally arranged to stimulate the right ventricle of the heart. It is also known to stimulate the left ventricle. In particular for the treatment of congestive heart failure (CHF) or other severe cardiac failures, it is known to stimulate the left ventricle, or both ventricles, in order to optimize the hemodynamic performance of the heart. Some of these monitoring or stimulation devices are arranged to sense an impedance between electrode surfaces that are positioned in or at the heart and which are connected to the device. The sensed impedance may be used to control different pacing parameters.

U.S. Pat. No. 4,733,667 describes a cardiac stimulator apparatus arranged with a lead that is preferably positioned in the right ventricle. The lead has a number of electrodes. The apparatus generates a signal corresponding to the impedance between two electrodes. The apparatus also includes a differentiator that produces a first derivative of this signal. The apparatus also has a peak detector that identifies the peak value of the first derivative on a beat-by-beat basis. The variation of this peak value is used to control the pacing rate. The pacing rate is thereby adapted to the level of exercise of the patient carrying the cardiac stimulator.

U.S. Pat. No. 5,720,768 describes different possible electrode positions in order to stimulate or sense the different chambers of the heart.

U.S. Pat. No. 5,154,171 describes the use of impedance values to control the pacing rate. The pacer described in this document is only arranged to stimulate the right side of the heart.

U.S. Pat. No. 6,070,100 teaches that electrodes may be positioned in both the left and the right atrium as well in the left and the right ventricle. The document describes the possibility of sensing the impedance between different electrodes. The sensed impedance values may be used to improve the cardiac output. The document mentions that a linear relationship exists between the peak dz/dt and the peak ejection rate.

Published U.S. application Ser. No. 2001/0,012,953 describes bi-ventricular pacing. An impedance may be measured between electrodes on the right and the left sides of the heart. The variation of the impedance with time is detected. The detected impedance variation may be used in order to synchronize the contraction of the ventricles.

Published U.S. application Ser. No. 2001/0,021,864 describes different manners of using the proximal and distal electrodes of different leads in order to inject a current and to measure an impedance. The measured impedance value may be used in order to maximize the cardiac flow.

It is often difficult to determine the specific cause of a heart problem. For example, for a patient suffering from congestive heart failure (CHF) it is often difficult to know what causes this problem. The cause may be a systolic dysfunction or a diastolic dysfunction. The systole relates to the contraction of the heart, i.e. the pumping phase. Diastole relates to the phase when the heart is relaxed, i.e. when the ventricles are being filled with blood.

SUMMARY OF THE INVENTION

An object of the present invention is to provide a device that makes it possible to determine, inter alia, a systolic dysfunction of the heart. A further object is to provide such a device that uses an impedance measurement when monitoring the function of the heart. A still further object is to provide such a device that in a relatively simple manner is able to determine a heart dysfunction. The device may also be arranged to deliver stimulation pulses to the heart in order to treat the determined dysfunction. A further object is to provide a system including such a device and a manner of using such a system.

These objects are achieved in accordance with the invention by a heart monitoring device having a control circuit, the control circuit being adapted to be electrically connected to a first electrode surface arranged at a first position of the heart and to a second electrode surface arranged at a second position of the heart, and the control circuit deriving an impedance value indicative of the impedance between said first and second electrode surfaces, determining a negative rate of change of this impedance value at a first point or portion of a heart cycle, monitoring the negative rate of change over a number of heart cycles, determining whether the negative rate of change, or its absolute value, increases or decreases over the aforementioned number of heart cycles.

By determining an appropriate impedance value and by monitoring the mentioned negative rate of change of the impedance value, an indication of the diastolic function of the heart is achieved. This will be explained below. With such a device it is thus possible to monitor and detect a possible diastolic dysfunction of the heart. A basis for treatment of the heart thus may be obtained. By determining whether this rate of change increases or decreases it is possible to decide whether the diastolic function of the heart is improved or gets worse.

In an embodiment, the control circuit also controls delivery of electrical stimulation pulses, via one or more electrical leads, to the heart. Preferably, the control circuit controls the delivery of these electrical stimulation pulses in response to the monitored value of the negative rate of change. By controlling the delivery of electrical stimulation pulses in response to the monitored value, a suitable treatment of the heart may be carried out.

In a further embodiment, the control circuit controls the delivery of the electrical stimulation pulses such that the diastolic time quotient is controlled in response to the monitored value of the negative rate of change (for a definition of the diastolic time quotient, see later in this description). Preferably, the diastolic time quotient is increased if the absolute value of said negative rate of change decreases. The diastolic time quotient preferably is decreased if the absolute value of said negative rate of change increases. By setting appropriate pacing parameters in response to the monitored value, an appropriate diastolic time quotient is achieved and thus an appropriate electrical stimulation of the heart is obtained. The diastolic time quotient thus may be controlled such that the heart has an appropriate time to relax such that the ventricles can be filled with blood.

In a further embodiment, the control circuit controls, within the same cycle of the heart, the delivery of stimulation pulses suitable to stimulate both the left and the right ventricles of the heart. When for example treating a patient suffering from CHF it is particularly important to stimulate both the ventricles of the heart in order to improve the heart condition of the patient.

In a further embodiment, the device has a housing, and the control circuit is contained in the housing and the device is designed to be implantable in a human or animal being. The device may thus for example constitute an implantable pacer.

The above objects also are achieved in accordance with the invention by a heart monitoring device having a control circuit adapted to be electrically connected to a first electrode surface arranged at a first position of the heart and to a second electrode surface arranged at a second position of the heart, the control circuit deriving an impedance value indicative of the impedance between said first and second electrode surfaces, determining a negative rate of change of this impedance value at a first point or portion of a heart cycle, determining a positive rate of change of the impedance value at a second point or portion of the heart cycle, determining a relationship between the positive rate of change and the negative rate of change, and monitoring this relationship over a number of heart cycles.

According to this version of the invention, the device thus monitors the aforementioned relationship between the positive and negative rates of change. By monitoring this relationship, the monitored values are less sensitive to other factors, such as amplitude variations of the impedance due to the breathing of the person or animal in question or variations in temperature. However, it should be noted that it is also within the scope of the invention to monitor both the mentioned relationship and the negative rate of change as described above.

According to a preferred embodiment, the relationship monitored by the control circuit is the ratio between the positive rate of change and the negative rate of change. Preferably, the control circuit also determines whether this ratio, or its absolute value, increases or decreases over the aforementioned number of heart cycles. By monitoring this ratio it is possible to determine whether the diastolic function of the heart is improved or gets worse. It should be noted that as used herein monitoring the ratio between the positive rate of change and the negative rate of change also includes the possibility of instead monitoring the inverse reciprocal of this ratio. An increase in the aforementioned ratio is of course equivalent to a decrease of the inverse, and vice versa.

In another embodiment, the control circuit controls delivery of electrical stimulation pulses, via one or more electrical leads, to the heart. It is thereby possible to deliver suitable stimulation pulses in order to improve the heart condition.

The control circuit controls the delivery of the electrical stimulation pulses in response to the monitored relationship. By controlling the delivery of electrical stimulation pulses in response to the monitored relationship, a suitable treatment of the heart may be carried out. Preferably, the systolic time quotient is controlled in response to the monitored relationship (a definition of the systolic time quotient is provided below).

According to a preferred embodiment, the systolic time quotient is increased if the absolute value of the ratio between the positive rate of change and the negative rate of change decreases. Analogously, the systolic time quotient is decreased if the absolute value of the ratio between the positive rate of change and the negative rate of change increases. By setting appropriate pacing parameters in response to the monitored relationship, an appropriate systolic time quotient is achieved and thus an appropriate electrical stimulation of the heart is obtained. The systolic time quotient thus is controlled such that the heart has an appropriate time in order to be able to pump out the blood from the ventricles. Through these features, the heart condition is improved.

The control circuit can control, within the same cycle of the heart, the delivery of stimulation pulses suitable to stimulate both the left and the right ventricles of the heart. When treating a patient suffering from CHF, for example, it is particularly important to stimulate both the ventricles of the heart in order to improve the heart condition of the patient.

The control circuit may be contained in a housing, with the device designed to be implantable in a human or animal being. The device thus, for example, may be an implantable pacer that may treat a patient suffering from, inter alia, CHF.

The above objects also are achieved by a heart monitoring system including a heart monitoring device according to any of the preceding embodiments and a first lead having at least the aforementioned first electrode surface and a second lead having at least the aforementioned second electrode surface, with the first and second leads being connected to the heart stimulating device such that the first and second electrode surfaces are connected to the control circuit. The system thus includes the device with attached first and second leads.

The invention also is directed to different ways of using such a system. The system can be employed so that a possible systolic dysfunction of said heart is monitored and treated. These ways of using the system thus concern the treatment of a human or animal being with the help of the system. Through such a treatment, inter alia, the heart condition of a patient suffering from CHF may be improved. In particular, the treatment may be carried out in response to a detected diastolic dysfunction of the heart.

DESCRIPTION OF THE PREFERRED EMBODIMENTS

Figure 1:
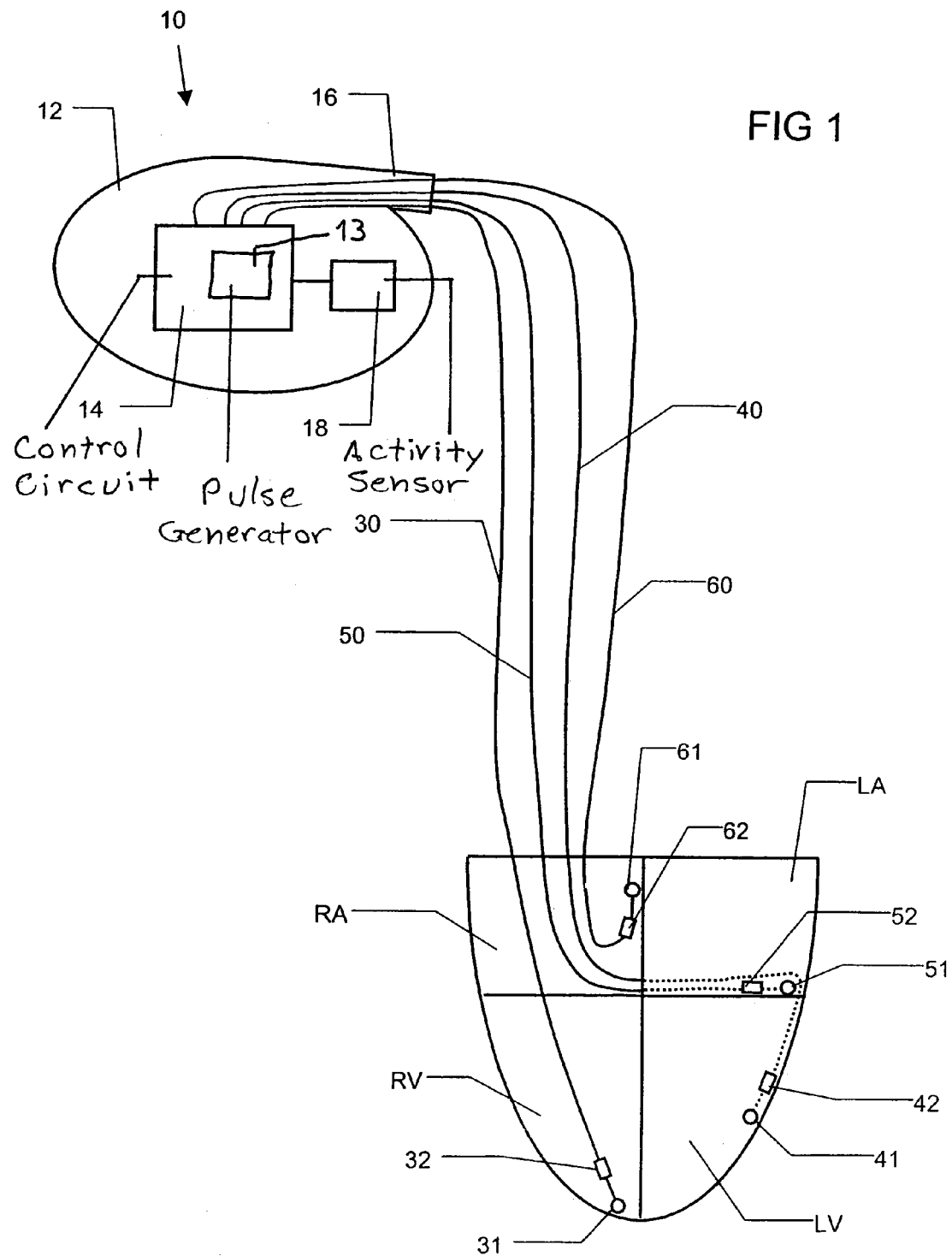
FIG. 1 schematically illustrates a heart monitoring device according to the invention connected to leads with electrode surfaces positioned in a heart.

An embodiment of the invention will now first be described with reference to FIG. 1. FIG. 1 schematically shows a heart monitoring device 10. According to a preferred embodiment, the device 10 has a housing 12. The device may be designed such that it can be implanted in a human or animal being. A control circuit 14 is arranged in the housing 12. The device 10 has a connector portion 16 to which a plurality of leads 30, 40, 50, 60 may be attached. In the shown embodiment there are thus four leads 30, 40, 50, 60 attached to the device 10. However, the number of leads may be less than four. In the shown embodiment, the first lead 30 comprises a distal electrode 31 (also called tip electrode) and a proximal electrode 32 (also called ring electrode). In the shown embodiment, the lead 30 is thus bipolar. However, it is also possible that one or more leads are unipolar, i.e. only having one electrode surface. The lead 30 includes electrical conductors (not shown) through which the electrode surfaces 31, 32 are connected to the control circuit 14. The control circuit 14 is also adapted to be connected to a second lead 40, which has corresponding electrode surfaces 41, 42.

The device 10 may also be arranged such that it is connectable to further leads. FIG. 1 thus shows a third lead 50 with electrode surfaces 51, 52 and a fourth lead 60 with electrode surfaces 61, 62.

FIG. 1 also schematically shows a heart having a right atrium RA, a right ventricle RV, a left atrium LA and a left ventricle LV. In the illustrated embodiment the electrodes 31, 32 are positioned in the heart near the apex of the right ventricle RV. The lead 40 is positioned such that the electrodes 41, 42 may be used for emitting stimulating pulses to the left ventricle LV. The lead 40 may for example be introduced through the right atrium RA, via the coronary sinus into the middle or great cardiac vein. In the shown embodiment, a third lead 50 is introduced such that the electrodes 51, 52 are positioned in the coronary sinus, a fourth lead 60 is introduced such that the electrodes 61, 62 are positioned in the right atrium RA. These manners of positioning the different leads 30, 40, 50, 60 are well known to those skilled in the art. All of these positions are defined herein as intracardiac positions.

The control circuit 14 derives an impedance value Z indicative of the impedance Z between two electrode surfaces. According to an embodiment, the impedance Z is sensed between electrode surfaces of two different leads. For example, the control circuit 14 may via the connector portion 16, sense an impedance between an electrode surface 31, 32 of the first lead 30 and an electrode surface 41, 42 of the second lead 40. The impedance may be sensed between the ring or tip electrode surfaces as described in some of the above mentioned documents. In an embodiment, the impedance value Z may be sensed between the electrode surfaces 32 and 42. The impedance may be measured, for example, by injecting a current and measuring a voltage in response to the injected current. Examples of how to measure the impedance are given in some of the above mentioned documents.

In an embodiment of the invention, the control circuit 14 also contains a pulse generator 13 that delivers electrical stimulation pulses, via one or more of the leads 30, 40, 50, 60, to the heart. The device according to this embodiment thus functions as a pacer. Such a pacer 10 is well known to a person skilled in the art and will therefore not be described in all its details here. The pulse generator 13 of the control circuit 14 may deliver stimulation pulses within the same cycle of the heart, suitable to stimulate both the left LV and the right RV ventricles of the heart. Such a device 10 may be used in order to treat, for example, a patient suffering from CHF.

The device 10 may also be arranged to receive signals indicating the activity level of a living being into which the device 10 is implanted. Such signals may for example be produced by an activity sensor 18 included within the housing 12. Different kinds of activity sensors 18 are known to those skilled in the art. Such an activity sensor 18 may be used to control different pacing parameters.

According to the invention, the control circuit 14 determines a negative rate of change $dZ_2/dt$.

Figure 2:
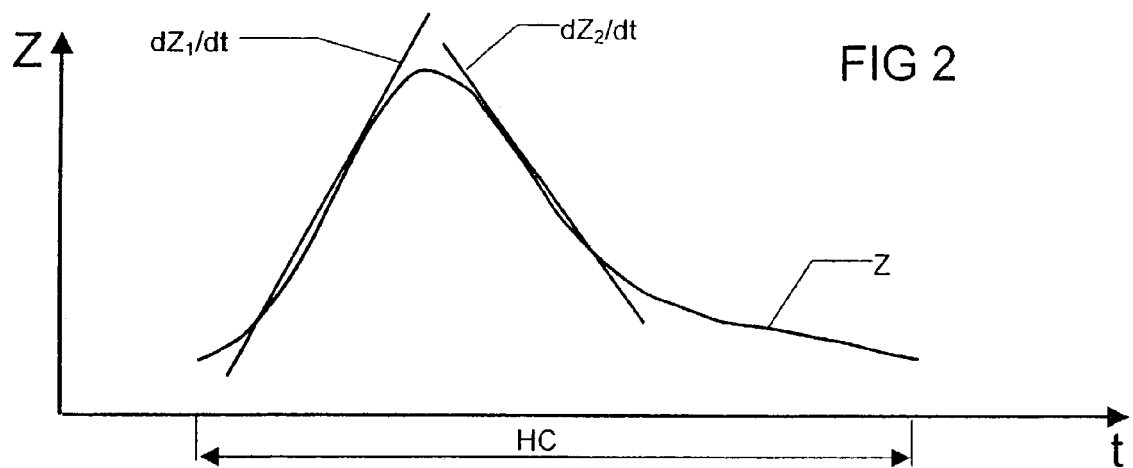
FIG. 2 schematically illustrates the variation of cardiac impedance over time.

The impedance variation during a heart cycle HC will now be explained with reference to FIG. 2, 3 and 4. FIG. 2 thus shows schematically the variation of the impedance Z with time t during a heart cycle HC. The impedance value here shown may be the impedance measured across the left ventricle LV of the heart. Such an impedance value may thus for example be obtained between the electrode surfaces 32 and 42 in FIG. 1. The impedance value Z is low when the ventricle LV is filled with blood. During the systolic phase, when the ventricle LV pumps out the blood, the impedance Z increases to a maximum value, whereafter the impedance Z drops when the ventricle LV fills with blood during the diastolic phase. FIG. 2 shows an indicated positive rate of change $dZ_1/dt$ of the sensed impedance value Z during the systolic phase. $dZ_2/dt$ represents a negative rate of change during the diastolic phase. $dZ_1/dt$ and $dZ_2/dt$ may be defined in different manners. For example, $dZ_1/dt$ may be the maximum of the derivative dZ/dt during the heart cycle. However, $dZ_1/dt$ may also be defined as an average positive rate of change during a certain portion of the heart cycle HC. Independently of how the positive rate of change is defined, this rate of change indicates the steepness of the curve Z during the systolic phase. $dZ_2/dt$ may be defined in analogous manners. Independently of exactly how $dZ_2/dt$ is defined, it represents the steepness of the curve Z during the diastolic phase.

Figure 3:
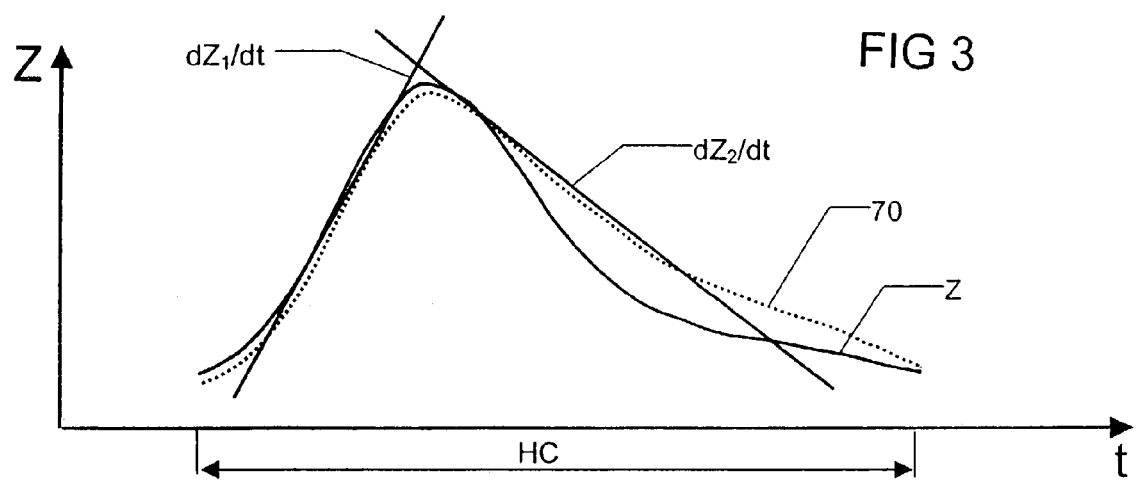
FIG. 3 shows the same representation as FIG. 2 but with an additional curve indicating a diastolic dysfunction.

FIG. 3 shows the same curve Z as FIG. 2. FIG. 3 also shows, with hatched lines, a second impedance curve 70. This curve 70 shows the impedance variation during a heart cycle when the diastolic function of the heart in question has become worse. As can be seen in FIG. 3, $dZ_1/dt$ is very similar to $dZ_1/dt$ in the case of the curve in FIG. 2. However, the curve 70 is flatter in the diastolic phase. Therefore, $dZ_2/dt$ is now not as steep as according to the curve Z in FIG. 2. The steepness of the negative rate of change $dZ_2/dt$ may thus be used as an indication of the diastolic function of the heart.

Figure 4:
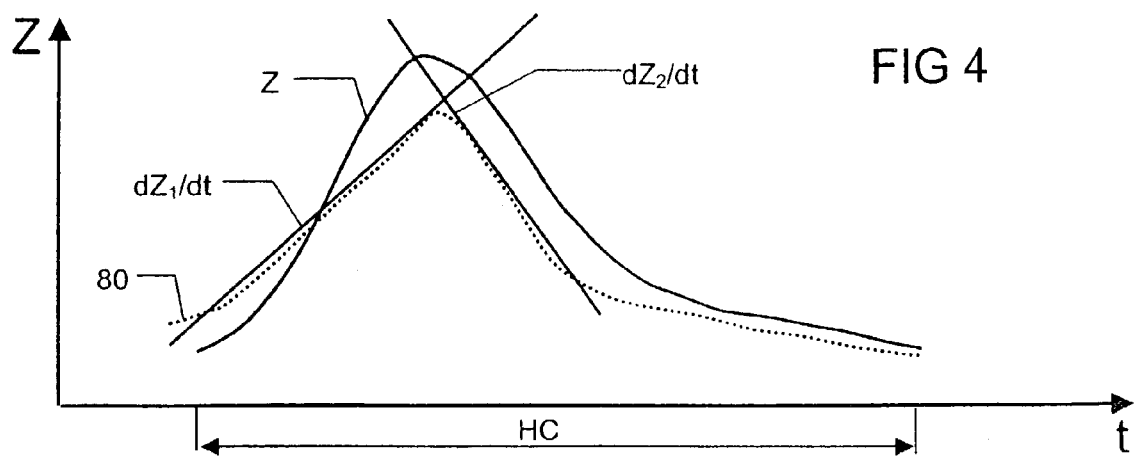
FIG. 4 shows the same representation as FIG. 2 but with an addition curve indicating a systolic dysfunction.

FIG. 4 shows the same curve Z as FIG. 2. Additionally, FIG. 4 shows in hatched lines a curve 80. This curve 80 represents the impedance value during a heart cycle HC when the systolic function of the heart has become worse compared to the situation in FIG. 2. The negative rate of change $dZ_2/dt$ is here quite similar to that of the curve Z in FIG. 2. However, the positive rate of change of $dZ_1/dt$ is now less steep than in FIG. 2. The steepness of $dZ_1/dt$ in FIG. 4 thus indicates that the systolic function of the heart has become worse compared to the situation in FIG. 2.

Figure 5:
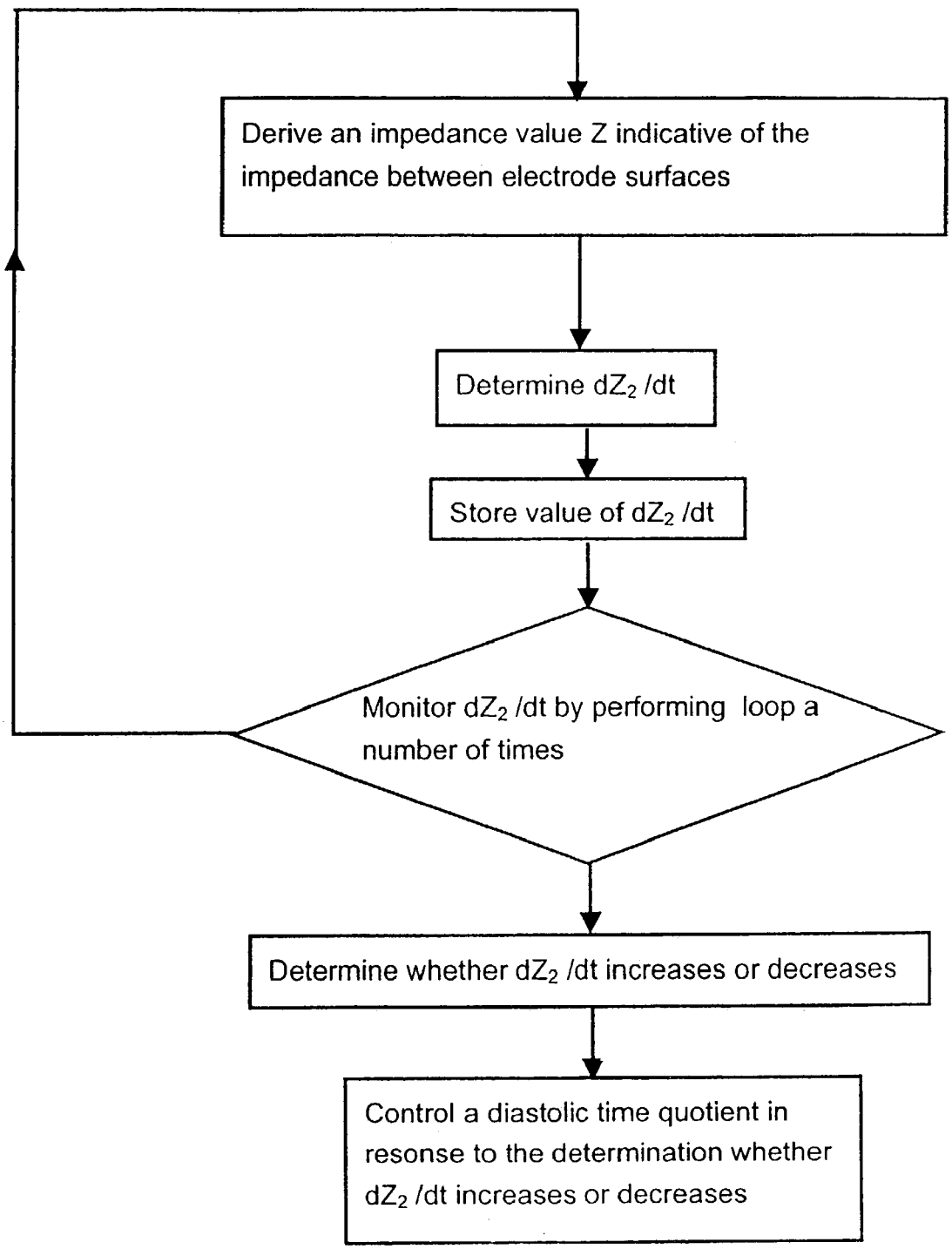
FIG. 5 is a flow chart of a function of the heart monitoring device that can be included in an embodiment of the invention.

FIG. 5 shows a flow chart of an operation of the device 10 that can be included in an embodiment of the invention. The control circuit 14 is arranged to derive an impedance value indicative of the impedance between first and second electrode surfaces, for example between the mentioned electrode surfaces 32 and 42. $dZ_1/dt$ is determined. The determined value of $dZ_1/dt$ is stored. $dZ_1/dt$ is monitored during a number of heart cycles HC. $dZ_1/dt$ may be continuously monitored all the time. Alternatively, it is possible monitor $dZ_1/dt$ only during certain periods. Since $dZ_1/dt$ is monitored, it is possible to determine whether $dZ_1/dt$ increases or decreases. It is thereby possible to derive information about the systolic function of the heart. In case the device 10 is arranged to deliver stimulation pulses to the heart, the systolic time quotient may be controlled in response to the determination whether $dZ_1/dt$ increases or decreases (in addition to the below exemplified manner of controlling the operation in response to the monitored relationship). The systolic time quotient can be defined as: $t_{systole}/(t_{systole}+t_{diastole})$ where $t_{systole}$ is the time of the systolic part of the heart cycle and $t_{diastole}$ is the time of the diastolic part of the heart cycle. The systolic time quotient is thus related to the systolic time in a pacer-controlled heart. The systolic time quotient may thus be controlled or varied by controlling different pacing parameters, for example the so-called AV-interval and/or the pacing rate and/or the VV-interval in a device that is able to deliver stimulating pulses to both the ventricles of the heart. If a worsening systolic function of the heart is detected, it is thus for example possible to increase the systolic time quotient in order to give the ventricles more time to pump out the blood.

It should be mentioned that the controlled value $dZ_2/dt$ may also be the absolute value of $dZ_2/dt$ in order to always have a positive value. The control circuit 14 may thus be arranged to increase the diastolic time quotient if the absolute value of $dZ_2/dt$ decreases. The control circuit 14 may be arranged to decrease the diastolic time quotient if the absolute value of $dZ_2/dt$ increases.

Figure 6:
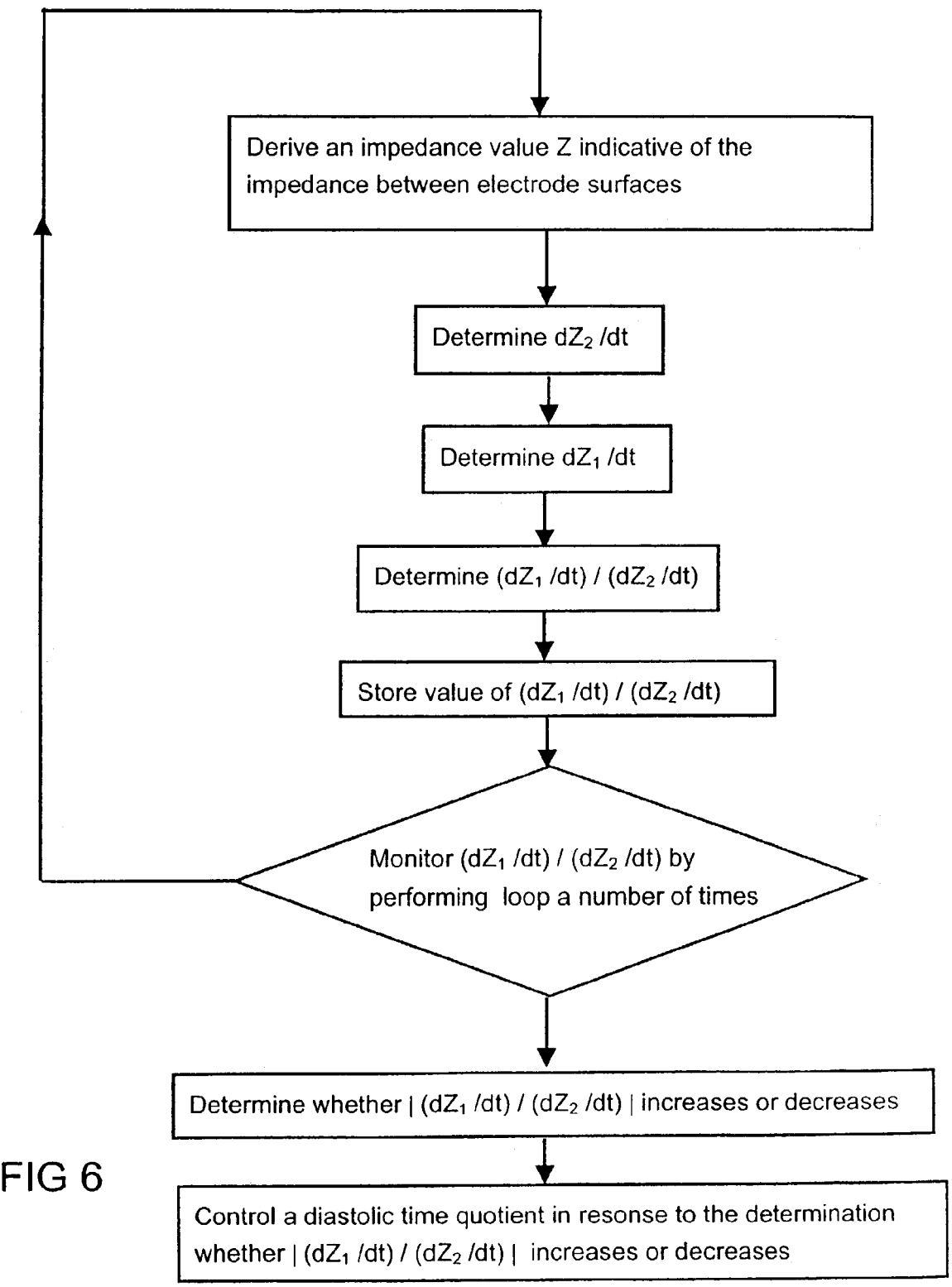
FIG. 6 is a flow chart of the function of the heart monitoring device according to an embodiment of the invention.

FIG. 6 illustrates schematically a flow chart of the operation of the device 10 according to an embodiment of the invention. An impedance value Z is derived. The impedance value Z is indicative of the impedance between electrode surfaces, for example between the electrode surfaces 32 and 42. Both $dZ_1/dt$ and $dZ_2/dt$ are determined. A relationship between the determined values is determined. This relationship may be the ratio $(dZ_1/dt)/(dZ_2/dt)$. Alternatively, the absolute value of this ratio may be determined. The value of the relationship or ratio is stored. This relationship is monitored over a number of heart cycles. This can be done in different manners as indicated above in connection with FIG. 5. The mentioned ratio is less sensitive to external influence on the impedance value Z than if only the positive change of rate $dZ_1/dt$ is monitored. The monitored value of $(dZ_1/dt)/(dZ_2/dt)$ indicates the function of the heart. It may be determined whether the absolute value of the mentioned ratio increases or decreases. The systolic time quotient may be controlled in response to the determined ratio in an analogous manner to that which has been described above in connection with FIG. 5. It is thus possible to decrease or increase the systolic time quotient in response to the monitored relationship. If the absolute value of the mentioned ratio decreases, the systolic time quotient may be increased and vice versa. The control circuit 14 may be arranged to enable the delivery of stimulation pulses to both the left LV and the right RV ventricles.

It should be mentioned that it is possible to arrange the control circuit 14 to monitor both the aforementioned ratio and the value $dZ_1/dt$. It is of course also possible at the same time to monitor the value $dZ_2/dt$. By the combined monitoring of these different values, a clear indication of whether the systolic function or the diastolic function of the heart changes is obtained. At the same time the influence on the impedance variation Z by external factors is reduced since the mentioned ratio is taken into account.

A heart monitoring system according to the invention is also illustrated in FIG. 1. This system comprises the device 10 according to any of the above embodiments together with at least a first lead 30 and a second lead 40. These leads 30, 40 are connected to the device 10 such that at least a first 31, 32 and a second 41, 42 electrode surface are connected to the control circuit 14. According to a manner of using such a system, the first 31, 32 and the second 41, 42 electrode surfaces are positioned in or at a heart of a human or animal being. The electrode surfaces 31, 32, 41, 42 may be introduced into the heart in the above described manner. The system is used such that the ratio $(dZ_1/dt)/(dZ_2/dt)$ is monitored in the manner described in connection with FIG. 6. Additionally, also the value $dZ_1/dt$ can be monitored as discussed in connection with FIG. 5. Advantageously, the electrode surfaces 31, 32, 41, 42 are positioned such that the impedance value Z is measured across at least a part of one of the first RV and second LV ventricles of the heart. Preferable, the impedance value Z is measured across the left ventricle LV of the heart. The system is preferably used to monitor a possible systolic dysfunction of the heart as has been described above. The system is particularly suitable to monitor a possible systolic dysfunction in a patient suffering from CHF. The system may be set up to deliver electrical stimulation pulses to the heart and to control the delivery of these pulses such that the systolic time quotient is controlled. Preferably, the system is used such that electrical stimulation pulses are delivered to both the ventricles RV, LV of the heart.

Different modifications are possible. For example, although the above described embodiments are directed to sensing an impedance value Z across the left ventricle LV of the heart is instead possible to detect an impedance value across the right ventricle RV. The mentioned rates of change may in this case be used to control the systolic time quotient also in case the device 10 is arranged to deliver stimulation pulses only to the right side of the heart.

Although further modifications and changes may be suggested by those skilled in the art, it is the intention of the inventors to embody within the patent warranted hereon all changes and modifications as reasonably and properly come within the scope of their contribution to the art.

We claim as our invention:

1. A heart monitoring device comprising:

a control circuit having an electrical connection adapted for electrical connection to a first electrode surface at a first in vivo intracardiac position relative to a heart and to a second electrode surface at a second in vivo intracardiac position relative to the heart; and said control circuit deriving an impedance value indicative of an in vivo cardiac impedance between said first and second electrode surfaces, determining a linear representation of a negative rate of change of said impedance value at a first portion of a heart cycle of the heart, monitoring said linear representation of said negative rate of change over a plurality of heart cycles of the heart, and determining whether said linear representation of said negative rate of change increases or decreases over said plurality of heart cycles as an indicator of at least one of systolic or diastolic dysfunction of the heart, and said control circuit generating an electrical control signal corresponding to said indicator, in a form suitable for controlling pacing of the heart.

2. A heart monitoring device as claimed in claim 1 wherein said control circuit determines whether the absolute value of said linear representation of said negative rate of change increases or decreases over the plurality of heart cycles of the heart.

3. A heart monitoring device as claimed in claim 1 further comprising a housing in which said control circuit is disposed, said housing being adapted for implantation in a living subject.

4. A heart monitoring device comprising:
a control circuit having an electrical connection adapted for electrical connection to a first electrode surface disposed at a first in vivo intracardiac position of a heart and to a second electrode surface disposed at a second in vivo intracardiac position of the heart; and
said control circuit deriving an impedance value indicative of an in vivo intracardiac impedance between said first electrode surface and said second electrode surface, determining a linear representation of a negative rate of change of said impedance value at a first portion of a heart cycle, determining a linear representation of a positive rate of change of said impedance value at a second portion of a heart cycle, determining a relationship between said linear representation of said positive rate of change and said negative rate of change, and monitoring said relationship over a plurality of heart cycles as an indicator of at least one of systolic or diastolic dysfunction of the heart, and said control circuit generating an electrical control signal corresponding to said indicator, in a form suitable for controlling pacing of the heart.

5. A heart monitoring device as claimed in claim 4 wherein said control circuit determines, as said relationship, a ratio between said linear representation of said positive rate of change and said linear representation of said negative rate of change.

6. A heart monitoring device as claimed in claim 5 wherein said control circuit determines whether said ratio increases or decreases over said plurality of heart cycles.

7. A heart monitoring device as claimed in claim 6 wherein said control circuit determines whether the absolute value of said ratio increases or decreases over said plurality of heart cycles.

8. A heart monitoring device as claimed in claim 4 further comprising a housing in which said control circuit is disposed, said housing being adapted for implantation in a living subject.

9. A heart monitoring system comprising:
a first electrode lead having a first electrode surface adapted for placement at a first in vivo intracardiac position of a heart;
a second electrode lead having a second electrode surface adapted for placement at a second in vivo intracardiac position of the heart; and
a control circuit electrically connected to said first and second leads, said control circuit deriving an impedance value indicative of an in vivo intracardiac impedance between said first and second electrode surfaces, determining a linear representation of a negative rate of change of said impedance value at a first portion of a heart cycle of the heart, monitoring said linear representation of said negative rate of change over a plurality of heart cycles of the heart, and determining whether said linear representation of said negative rate of change increases or decreases over said plurality of heart cycles as an indicator of at least one of systolic or diastolic dysfunction of the heart, and said control circuit generating an electrical control signal corresponding to said indicator, in a form suitable for controlling pacing of the heart.

10. A heart monitoring system as claimed in claim 9 wherein said control circuit determines whether the absolute value of said linear representation of said negative rate of change increases or decreases over the plurality of heart cycles of the heart.

11. A heart monitoring system as claimed in claim 9 wherein said control circuit comprises a pulse generator and delivers electrical stimulation pulses to the heart from the pulse generator via at least one of said first and second electrode leads dependent on said control signal.

12. A heart monitoring system as claimed in claim 11 wherein said control circuit controls the delivery of said electrical stimulation pulses by using said control signal to control a systolic time quotient associated with the heart dependent on said control signal.

13. A heart monitoring system as claimed in claim 12 wherein said control circuit increases said systolic time quotient if the absolute value of said linear representation of said negative rate of change decreases.

14. A heart monitoring system as claimed in claim 12 wherein said control circuit decreases said systolic time quotient if the absolute value of said linear representation of said negative rate of change increases.

15. A heart monitoring system as claimed in claim 9 wherein first and second electrode lead, are respectively adapted to be disposed in a left ventricle and a right ventricle of the heart, and wherein said control circuit comprises a pulse generator and, within each of said plurality of cycles, delivers stimulation pulses from said pulse generator respectively via said first and second electrode leads, dependent on said control signal, to stimulate said left ventricle and said right ventricle.

16. A heart monitoring system as claimed in claim 9 further comprising a housing in which said control circuit is disposed, said housing being adapted for implantation in a living subject.

17. A heart monitoring system comprising:
a first electrode lead having a first electrode surface adapted for placement at a first in vivo intracardiac position of a heart;
a second electrode lead having a second electrode surface adapted for placement at a second in vivo intracardiac position of the heart; and
a control circuit electrically connected to said first and second leads, said control circuit deriving an impedance value indicative of an in vivo intracardiac impedance between said first electrode surface and said second electrode surface, determining a linear representation of a negative rate of change of said impedance value at a first portion of a heart cycle, determining a linear representation of a positive rate of change of said impedance value at a second portion of a heart cycle, determining a relationship between said linear representation of said positive rate of change and said linear representation of said negative rate of change, and monitoring said relationship over a plurality of heart cycles as an indicator of at least one of systolic or diastolic dysfunction of the heart, and said control circuit generating an electrical control signal corresponding to said indicator, in a form suitable for controlling pacing of the heart.

18. A heart monitoring system as claimed in claim 17 wherein said control circuit determines, as said relationship, a ratio between said linear representation of said positive rate of change and said linear representation of said negative rate of change.

19. A heart monitoring system as claimed in claim 18 wherein said control circuit determines whether said ratio increases or decreases over said plurality of heart cycles.

20. A heart monitoring system as claimed in claim 19 wherein said control circuit determines whether the absolute value of said ratio increases or decreases over said plurality of heart cycles.

21. A heart monitoring system as claimed in claim 17 wherein said control circuit comprises a pulse generator and delivers electrical stimulation pulses to the heart via at least one of said first and second electrode leads dependent on said control signal.

22. A heart monitoring system as claimed in claim 21 wherein said control circuit controls the delivery of said electrical stimulation pulses by usina said control signal to control a systolic time quotient associated with the heart dependent on said relationship.

23. A heart monitoring system as claimed in claim 22 wherein said control circuit determines, as said relationship, a ratio between said linear representation of said positive rate of change and said linear representation of said negative rate of change, and wherein said control circuit increases said systolic time quotient if the absolute value of said ratio decreases.

24. A heart monitoring system as claimed in claim 22 wherein said control circuit decreases said systolic time quotient if the absolute value of said ratio increases.

25. A heart monitoring system as claimed in claim 17 wherein said first and second electrode lead, are respectively adapted to be disposed in a left ventricle and a right ventricle of a heart, and wherein said control circuit comprises a pulse generator and, within said plurality of cycles, delivers stimulation pulses from said pulse generator respectively via said first and second electrode leads, dependent on said control signal, to stimulate said left ventricle and said right ventricle.

26. A heart monitoring system as claimed in claim 17 further comprising a housing in which said control circuit is disposed, said housing being adapted for implantation in a living subject.

27. A method for monitoring a heart comprising the steps of:
  (a) placing a first electrode surface at a first in vivo intracardiac position of a heart;
  (b) placing a second electrode surface at a second in vivo intracardiac position of the heart;
  (c) automatically electronically deriving an impedance value indicative of an in vivo intracardiac impedance between said first and second electrode surfaces;
  (d) automatically electronically determining a linear representation of a negative rate of change of said impedance value at a first portion of a heart cycle of the heart;
  (e) automatically electronically monitoring said linear representation of said negative rate of change over a plurality of heart cycles of the heart; and
  (f) a degree of at least one of systolic or diastolic dysfunction of the heart from automatically electronically determining whether said linear representation of said negative rate of change increases or decreases over said plurality of heart cycles of the heart, as a monitoring result; and
  (g) automatically generating and emitting an electrical control signal corresponding to said monitoring result in a form suitable for controlling pacing of the heart.

28. A method as claimed in claim 27 wherein steps (a) and (b) comprise positioning said first and second electrode surfaces to measure said impedance value across at least a part of a ventricle of the heart.

29. A method as claimed in claim 28 comprising measuring said impedance value across the left ventricle of the heart.

30. A method as claimed in claim 27 comprising using said relationship to monitor systolic dysfunction of the heart.

31. A method as claimed in claim 30 wherein steps (a) and (b) comprise placing said first and second electrodes in a heart of a patient suffering from congestive heart failure, and monitoring said systolic dysfunction as a symptom of said congestive heart failure.

32. A method as claimed in claim 30 comprising delivering electrical stimulation pulses to the heart to control a systolic time quotient of the heart dependent on said linear representation of said negative rate of change.

33. A method as claimed in claim 32 comprising delivering said stimulation pulses to each of the left ventricle and the right ventricle of the heart.

34. A method as claimed in claim 27 wherein step (d) comprises determining said linear representation of said negative rate of change of said impedance value at a first portion of said heart cycle and further comprises determining a linear representation of a positive rate of change of said impedance value at a second portion of said heart cycle.

35. A method as claimed in claim 34 wherein steps (a) and (b) comprise positioning said first and second electrode surfaces to measure said impedance value across at least a part of a ventricle of said heart.

36. A method as claimed in claim 35 comprising measuring said impedance value across the left ventricle of the heart.

37. A method as claimed in claim 34 wherein steps (a) and (b) comprise placing said first and second electrodes in a heart of a patient suffering from congestive heart failure, and monitoring said systolic dysfunction as a symptom of said congestive heart failure.

38. A method as claimed in claim 37 wherein the step of monitoring said systolic dysfunction comprises determining a ratio of said linear representation of said positive rate of change and said linear representation of said negative rate of change, and comprising delivering electrical stimulation pulses to the heart to control a systolic time quotient of the heart dependent on said ratio.

39. A method as claimed in claim 38 comprising delivering said stimulation pulses to each of the left ventricle and the right ventricle of the heart.

* * * * *